(12) United States Patent
Zhang

(10) Patent No.: US 9,365,813 B2
(45) Date of Patent: Jun. 14, 2016

(54) BIOREACTOR SYSTEM AND METHODS FOR ALTERNATIVE CELL CULTURE BETWEEN STATIC AND DYNAMIC

(71) Applicant: Yongxin Zhang, Carrollton, TX (US)

(72) Inventor: Yongxin Zhang, Carrollton, TX (US)

( * ) Notice: Subject to any disclaimer, the term of this patent is extended or adjusted under 35 U.S.C. 154(b) by 200 days.

(21) Appl. No.: 14/040,687

(22) Filed: Sep. 29, 2013

(65) Prior Publication Data

US 2015/0093819 A1   Apr. 2, 2015

(51) Int. Cl.
*C12M 1/02* (2006.01)
*C12M 1/12* (2006.01)
*C12M 3/04* (2006.01)
*C12M 1/42* (2006.01)

(52) U.S. Cl.
CPC ............... *C12M 25/16* (2013.01); *C12M 27/10* (2013.01); *C12M 35/00* (2013.01)

(58) Field of Classification Search
CPC ...... C12M 27/10; C12M 27/14; C12M 25/16; C12M 25/20; B01F 13/0809; B01F 13/0818
See application file for complete search history.

(56) References Cited

U.S. PATENT DOCUMENTS

2005/0054101 A1*   3/2005   Felder et al. ................... 435/383
2006/0019388 A1*   1/2006   Hutmacher et al. ........... 435/394

* cited by examiner

*Primary Examiner* — William H Beisner

(57) ABSTRACT

The invention relates to a bioreactor system characterized by its capacity in cultivating cells in all three states: static, dynamic, or alternating between static and dynamic states in the same cell culture container or containers, with the even distribution of cells in cell static culture following a dynamic culture. In the invented bioreactor system, the combined application of the magnetically controlled agitation and the cell culture container inversion as well as the combined application of the vertical rotating culture and horizontal static culture are the two strategies in building ideal bioreactors for the cell culture alternating between static and dynamic states in the same cell culture container, which can minimize the sheer-stress and provide cells an ideal metabolic environment.

8 Claims, 3 Drawing Sheets

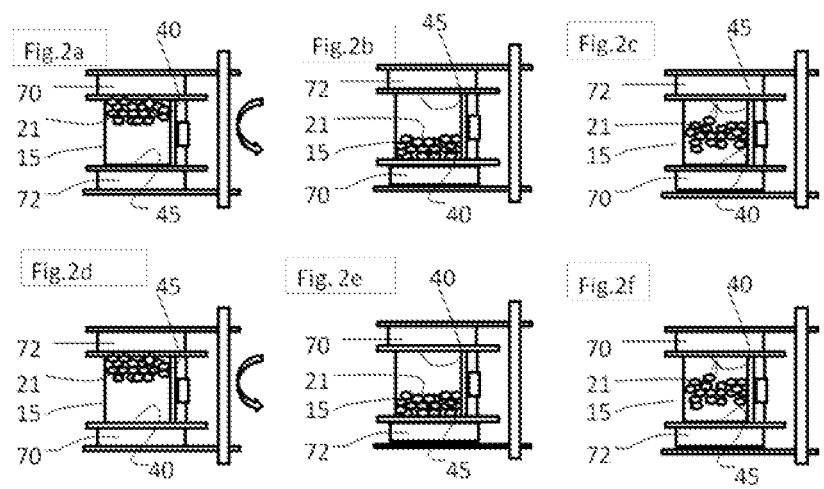

BIOREACTOR SYSTEM AND METHODS FOR ALTERNATIVE CELL CULTURE BETWEEN STATIC AND DYNAMIC

FIELD OF THE INVENTION

The invention relates to a bioreactor for cultivating cells in three possible states: static, dynamic, or alternating between static and dynamic states in the same cell culture container(s).

BACKGROUND OF THE INVENTION

This application relates generally to bioreactors and more particularly bioreactors for growing cells in three possible states: static, dynamic, or alternating between static and dynamic states in the same cell culture container(s).

Many kinds of cells, especially hematopoietic stem cells and immunocytes, are very sensitive to shear-stress in the culture. For example, shear-stress can cause the non-specific differentiation and the increased apoptosis in the stem cell culture, which significantly reduces the efficiency of the stem cell expansion and directed differentiation. The higher shear-stress also causes the more release of non-specific proteins in protein expression, in which the protein of interest takes less proportion in the culture and so result in the increased difficulties of protein purification. The static culture has the least shear stress but the cells in static culture normally sit at the bottom of the culture containers, some cells cannot get enough nutrition when cells are at higher density and so not suitable for large scale cell expansion. Some bioreactors, such as NASA's rotation wall vessel (RWV) bioreactor, were designed for reducing the shear-stress. However, these bioreactors have to keep cells in suspension by continuously moving, stirring or/and agitating cells. Once the bioreactor stop running, cells will accumulate or aggregate somewhere of the bottom of or other locations within the cell culture container but are not evenly distributed, which is harmful for most cell growth or at least is not conductive to efficient cell growth. Therefore, though the shear-stress has been reduced in these bioreactors, such a reduced shear-stress has to continuously exert on the cultured cells when these bioreactors are running. No doubt, an intermittent cell agitation, or the suitable alternation between static and dynamic culture, will not only minimize the sheer-stress but also provide cells an ideal metabolic environment. However, it is often very difficult to get cells evenly distributed in the static cell culture following a dynamic culture because of the inertia the moving cells have, while an uneven distribution (such as local accumulation or aggregation) of cells in static culture could be very harmful for cell growth as mentioned above. Our current invention provides some methods to allow cells to be evenly distributed in the static culture following a dynamic culture, so that all three cell culture states can be employed in present disclosed bioreactor system.

Some other bioreactors, such as those invented by Felder and colleagues, the static and dynamic states of the cell cultures are respectively performed in two or more different cell culture containers and the changes between the two states of the cell culture are carried out by transferring cell from one type of cell culture container to the other type of cell culture container. When cells are transferred between containers, the cell losses and damages are inevitable. In our current invention, both static and dynamic cell cultures are carried out in the same cell culture container(s), no cell-transferring between cell culture container is needed during the alternating between the two culture states, and when the cell culture is changed from the dynamic to the static status, cells can be evenly distributed at the bottom of the culture chamber (container) or on the surface of the stirring or supporting materials. Thus, our invention provides cells the best growth condition in both suspension states and static states, and these two states can repeatedly alternate.

Some bioreactors use magnet element (specifically blades or vans) controlled by magnet impeller to agitate culture media to keep cells in suspension status. This kind of bioreactor purposely enhances the shear-stress for the culture requirements of a certain cells and the cells are distributed following the direction of media flow agitated by the impellers when the agitation stops. The higher shear-stress and uneven distribution of the cells in static state following agitation make it significant different from our current invented bioreactor system. In addition to the differences in the application, the bioreactor in our invention does not use blades or canes to be the magnet element, and the magnet beads in our invention actually has no magnetism if they are not in magnet field and they can only gain magnetism when they are placed in magnet field. The magnet beads in our invention are not controlled by impeller but by the changes of magnetic strength affecting the beads' moving.

In one embodiment of our bioreactor, in order to minimize the sheer-stress during the agitation and allow the cells evenly distributed in the bioreactor, the agitators' movement between two ends of the interior cell culture container in combination with the corresponsive inversion of the cell culture container are applied in our current invented system. In comparison, other bioreactors either use agitators or use moving container to keep the cells suspended, and either of them does not allow the cells evenly distributed in the bioreactor following agitation and always exerts higher sheer-stress on cells in the culture. It also needs to be emphasized that the inversion of the cell culture container in our system is not for the cell suspension. Instead, the effects of the movement of the cell culture container on the cells suspension in this embodiment are intended to be minimized in our design, because the movement of the container often tends to result in uneven distribution of the cells in static culture. The inversion of cell culture container in our system mainly provides a suitable condition for the agitators to move from one end to the other end of the interior cell culture container.

In another embodiment of our bioreactor, the changes of cell culture states between static and dynamic are carried out by the changes between vertical rotating culture and horizontal static culture. The speed of the cell culture container rotation and the deceleration of the of the cell culture container from rotating to static state are two critical factors affecting cell distribution in static state. The higher or lower speed and deceleration of the cell culture container rotation can result in uneven distribution of the cells following rotation. In our research, the suitable speed and deceleration were founded.

In our research, we also found that both the time length of the static culture and dynamic culture and the frequency of the alternation between static culture and dynamic culture significantly affect the cell growth and need to be determined based upon the cell type, media, cell density (cell concentration) and cell doubling time (cell growth speed) for the specific cell culture.

In our previous patent application, some of the above embodiments have been mentioned but not clearly shown in the claims. In this application, they are all clearly claimed.

SUMMARY

The invention relates to a bioreactor system characterized by its capacity to cultivate cells in all three states: static, dynamic, and alternating between static and dynamic states in the same cell culture container(s), and emphasizes the even distribution of cells in cell static culture following a dynamic culture. In the invented bioreactor system, the combined application of the magnetically controlled agitation and the cell culture container inversion as well as the combined application of the vertical rotating culture and horizontal static culture are the two strategies in building the ideal bioreactors for the cell culture alternating between static and dynamic states in the same cell culture container, which can minimize the sheer-stress and provide cells an ideal metabolic environment.

Although the currently invented bioreactor system allows growth in all three culture states, especially in the alternation between static and dynamic, it can also used for either static cell culture or dynamic cell culture. In the dynamic cell culture, cells could be re-suspended by any methods, including but not limited to magnetic stirring and cell culture container rotation.

The even distribution of the cells in static culture said in this disclosure can be on the bottom of the cell culture container or on any materials on the bottom of the cell culture container, or any part of the interior cell culture container.

The cells cultivated by the currently invented bioreactor system include all types of suspension cells, adherent cells and partial adherent cells. When the adherent cells are cultured, they can be attached to a certain carriers.

The dynamic state of the bioreactor system in this disclosure induces conditions in which cells move within the medium, the medium moves around the cells, the culture container moves or any combination thereof. When the cells move in the media., adherent cells moves with the agitators or carriers on which these cells attach. For the smaller sheer-stress during the cell re-suspension or agitation, the applications of vertical movement of agitators and vertical rotation of cell culture containers are two of the options, and other methods may also be used in this bioreactor system for the intermittent cell suspension culture.

The static state of this bioreactor system includes any conditions in which cells do not move relative to the cell culture container, cell culture medium, the bioreactor or the environment in which the cell culture is being performed. In some cases, the cells attached to some carriers and these carriers may be located at the side walls of the container and do not move relative to the cell culture container, it could be considered as static culture though these cells are not at the bottom as in usual static culture.

The cell culture states in this bioreactor system can freely alternate between the dynamic stat and the static state, in which the alternations can occur at any time, speed, and frequency, which may be operated by the program. We have found the relationships among the period of static or dynamic culture, the frequency of the static and dynamic culture alternation, cell density, cell growth speed (doubling time), cell yield and the cell quality which was evaluated by the cell death and apoptosis and cell non-specific differentiation and engraftment potential for stem cells.

The current invented bioreactor system may comprise a combination of a cell culture container inversion and magnet agitation. In one embodiment, cells are re-suspended by some agitators which were controlled by electric magnet field. When agitators are moving up, cells are brought up by these agitators. When the agitators reach the top of the cell culture container, they are held by the electric magnet at that end. Then cell container will be inverted about 180° to position the agitators at the lower part (bottom) of the container following the inversion. These agitations of cells in this case may start before the inversion of the cell culture container. The cell container inversion mainly provides suitable position for the agitators to move up and down.

The current invented bioreactor system may also comprise a combination of cell culture container orientation for rotating culture and another culture container orientation mainly for static culture. In one embodiment, the cell container rotates vertically and keeps its static culture horizontally. For the even distribution of cells in the static culture, the speed of the rotation, the deceleration of the cell culture container rotation and the speed of its position change from vertical to horizontal as well as their relationships have their optimal ranges, although these ranges are not limited. The range for the optimal speed of the rotation is 2 rpm to 60 rpm, the range for the deceleration of the cell culture container is $-5$ rpm$^2$ to $-120$ rpm$^2$, the range for the ratio of the rotation speed/deceleration of the cell culture container rotation is 1 to 160, and the range for the speed of container position change is 0.1 to 60 rpm. In these ranges, cells can be or have significantly higher chance to be evenly distributed in the cell culture container in the static culture following a dynamic culture. In contrast, cells have significantly less chance to be or completely cannot be evenly distributed if the bioreactor setting is out of these ranges.

Although most bioreactors are controlled by computing system, since our current disclosed bioreactor system is capable to cultivate cells in all three states (static, dynamic, or alternating between static and dynamic states the static culture) in the same cell culture container(s), especially it can keep cells evenly distributed in static culture following a dynamic culture, the computing system controlling on this system for the three states adjustment is unique and important. The said computing control system includes all kinds of computers and similar automation devices which can be used to program the three states, especially used to program the alternation between static and dynamic states.

Cell culture container (vessel, chamber or sealed plate) in this invention can be made with any materials that are not harmful for the cell growth. It is preferable that at least one part of the cell culture container wall is made of the gas permeable material or dialysis membrane. The container has one or more ports serving as entrances or/and exits for cells, media, buffer, agitators and other materials, such as protein, cytokines, and other reagents, for cell growth and differentiation. The agitator can be in any shape, although a sphere in a suitable size is favorable. It could but not limited to be made of paramagnet (magnetizable) materials covered by some materials that are inert and good for cell growth and in some cases for cell attachment.

The bioreactor system has its power sets, which include but not limited to the engines, step motors, servo motors and so on. These power sets are used for most mechanical movement of any part of the bioreactor, including but not limited to the inversion and rotation of cell culture container, the adjustment of the vertical and horizontal level for the cell culture states. Although all operations can be performed manually, the application of the automation devices is preferred.

BRIEF DESCRIPTION OF THE DRAWINGS

The drawings, when considered in connection with the following description, are presented for the purpose of facilitating an understanding of the subject matter sought to be protected.

FIGS. 2a-2f show a series of schematic views of a bioreactor showing the movement of an agitator within a chamber in series;

DETAILED DESCRIPTION

Figure 1:
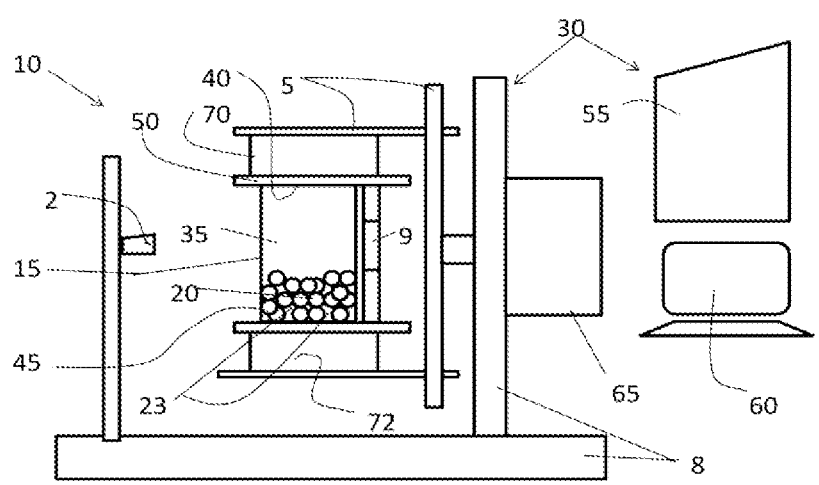
FIG. 1 is a schematic view showing an illustrative bioreactor.

Referring now to FIG. 1, a bioreactor system 10 for growing cells is shown. The system 10 includes a cell culture chamber 15, an agitator 20 and a control system 30.

The cell culture chamber 15 includes an interior 35 for receiving and growing target cells in a cell culture media disposed therein, a first end 40 and a second end 45. As used herein, "target cells" refers to cells disposed within the chamber 15 and which are grown within the chamber 15. While the present disclosure is given the context of growing target cells, it will be appreciated that the system may be employed to mix chemicals or any other suitable solution or material. Also, while the first end 40 and second end 45 are shown as being at the top and bottom of the chamber 15 respectively, it will be appreciated that the ends 40 and 45 may be in any suitable orientation relative to one another (e.g., in a horizontal plane) and remain within the scope of the present disclosure. As will be discussed below, the chamber 15 may include one or more interior compartments. In addition, as will be appreciated by those skilled in the art, the chamber 15 may be formed from any suitable material, including a rigid material, a flexible material, a combination of rigid and flexible materials, a gas permeable material or any other suitable material. The chamber 15 may further include one or more ports for providing fluid communication between the chamber interior 35 and one or more reservoirs. Illustrative reservoirs include, without limitation, a cell culture media reservoir, a waste reservoir, a buffer reservoir, a $CO_2$ reservoir, or any other suitable reservoir.

Referring now to FIG. 2a-2f, operation of the system 10 is illustrated by way of a non-limiting example. Target cells and cell culture media are delivered to the interior 35 of the chamber 15. In this embodiment, the beads 21 are buoyant and float near the top of the cell culture media within the chamber 15. In FIG. 2a, the first magnetic field generator 70 is energized and the beads 21 are held near the first end 40 of the chamber 15. The chamber 15 is then rotated approximately 180° to a position as shown in FIG. 2b wherein the first magnetic field generator 70 maintains the beads 21 near the chamber first end 40. Normally, cells are in suspension and gradually falling down to the surface of the beads 21 and the interspaces among the beads 21 to start static culture. After suitable incubation period based on the culture protocol, the first magnetic field generator 70 may be de-energized whereby the beads 21 begin to float towards the second end 45 of the chamber 15 to re-suspend the cells as shown in FIG. 2c. In embodiments where the beads 21 include a coating which target cells will adhere to, movement of the beads 21 from one end to the other will collect newly grown target cells. The target cells may adhere to the beads 21 while waste is flushed from the chamber 15 and/or when new media is introduced to the chamber 15 such that a substantial number of the target cells, original and newly grown, remain within the chamber. Alternatively, magnetizable antibodies specific to the target cells may be added to the interior of chamber 15 whereby the antibodies will bind themselves to the target cells, and when a magnetic field is introduced to the chamber, the antibody bound target cells will be releasably coupled to the magnetizable beads 21 and/or the chamber wall(s) adjacent to the magnetic field generator(s). In this embodiment, one or both of the magnetic field generators 70, 72 may remain energized while unbound cells and/or waste are flushed from the chamber and/or while new media is introduced to the chamber such that a substantial number of the target cells, original and newly grown, remain within the chamber 15. Alternatively, magnetic reagents, such as Annexin V or other suitable reagent, may be employed to couple to damaged or dead cells to the beads and the healthy target cells flushed from the system 10. Further, it will be appreciated that magnetizable antibodies and/or reagents may be employed in a chamber 15 without the use of an agitator whereby the target cells or damaged/dead cells may be held against the chamber when the chamber is flushed.

Referring again to FIGS., once the beads 21 are near the second end 45 of the chamber, the second magnetic field generator 72 may be energized whereby the beads 21 are held near the chamber second end 45 (FIG. 2d) and the chamber inverted to the position shown in FIG. 2e. The second magnetic field generator 72 may then be de-energized whereby the beads 21 will float towards the chamber first end 40 as shown in FIG. 2f. As will be appreciated by those skilled in the art, a variety of additives, media, buffers, $CO_2$ and the like may be selectively added to the chamber at any desired point during this process and/or waste selectively removed in order to promote or enhance new cell growth based on measurements taken by the control system as previously discussed. In this embodiments, the movement of beads 21 keeps the cells in suspension (dynamic) state, and when the beads 21 stop moving and keeps stay somewhere in the cell culture container (chamber), such as on the bottom of the chamber, cells slowly fall down and are evenly distributed on the surface of the beads 21 and the voids among the beads 21, from where the static cell culture starts.

In an alterative embodiment, non-buoyant beads may be employed such that the beads are moved within the chamber by rotation of the chamber and without also being subjected to magnetic fields. Here, gravity and centrifugal force, by way of rotation of the chamber, are employed to move the beads between two or more points within the chamber 15. In yet another alternate, the first and second magnetic field generators 70 and 72 may be alternately energized so as to move the beads between two or more points within the chamber and without any rotation of the chamber 15. While the forgoing example employs beads 21 as the agitator, it will be appreciated that suitable device may be employed as the agitator and remain within the scope of the present disclosure. Moreover, it will be appreciated that any means or technique for moving the agitator within the chamber may be employed and remain within the scope of the present disclosure.

Moreover, it will be appreciated that if the chamber 15 formed from gas permeable material or otherwise includes a gas permeable portion, the system may be disposed within a $CO_2$ incubator or $CO_2$ room. Without a $CO_2$ incubator or $CO_2$ room or without any gas permeable portion of the chamber, reagents, such as HEPES may be employed or, alternatively, $CO_2$ may be injected directly into the chamber from a $CO_2$ reservoir.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

The agitator 20 is disposed within the chamber interior 35 and is capable of moving between the chamber first end 40 and chamber second end 45. Alternatively, the agitator 20 may be configured to be moved between any two or more points, or between any two or more portions, within the chamber interior 35. In the illustrative embodiment, the agitator comprises a plurality of beads 21. It will be appreciated that any illustrative embodiment showing beads 21 may use any alternative agitator configuration and remain with the scope of the present disclosure and that any particular illustrative embodiment is not limited to using beads exclusively as the agitator. In one embodiment, the beads 21 are be formed from a magnetizable material, such as silicon steel, $Fe_3O_4$, or any other suitable magnetizable material. As used herein, magnetizable means that the agitator, such as the beads, will hold a magnetic charge when subjected to a magnetic field but will not otherwise hold a magnetic charge once removed from the magnetic field, or the magnetic field removed from the vicinity of the agitator, for example, when a magnetic field generator is de-energized. The magnetizable material typically comprises the core of each bead 21. The magnetizable core may then be coated with any suitable material. In one embodiment, the magnetizable core is coated with polystyrene; however, it will be appreciated that the magnetizable core may be coated with any suitable material and remain within the scope of the present disclosure. For example, and without limitation, the magnetizable core may be coated with any suitable thermoplastic or thermoset polymer. While the beads 21 are shown as being formed from a magnetizable material, it will be appreciated that the beads may be formed from any suitable material, magnetizable or non-magnetizable, and remain within the scope of the present disclosure. Additionally, it will be appreciated that the beads 21 may each be coated with any suitable material such that the target cells will adhere to the beads as the cells grow within the chamber 15, yet it will be appreciated that beads not coated with a particular material to which target cells will adhere also remain within the scope of the present disclosure. In some embodiments, it may be desirable to have beads 21 that are buoyant within the cell culture media; therefore, the core of the beads may include air pockets or bubbles, a lightweight foam or plastic or any other suitable material for permitting the beads 21 to be buoyant within the media.

The beads 21 may be formed such that one or more niches, or micoenvironments, may be formed or created in the voids between the beads 21 when the beads are stacked together. In some embodiments, these niches may promote growth of additional target cells therein. In one embodiment, where the beads are substantially spherical, the diameter or each bead 21 may be between 1 mm and 10 mm for the creation of suitable niches. However, it will be appreciated that the beads 21 may have any suitable size and/or shape such that one or more suitable niches may be formed when the beads 21 are stacked together. Also, it will be appreciated that at least some niches may be formed between some beads and one or more walls of the chamber interior.

Referring again to FIG. 1, the control system 30 may include one or both of a controller 55 and computer 60 for controlling operation of the system 10. Alternatively, the system 10 may be run manually. The control system 30 is configured to be releasably coupled to the chamber 15. The control system 30 may include a cassette 50 for receiving the chamber 15 but it will be appreciated that the chamber 15 may be coupled to the control system 50 via any suitable means or configuration (e.g., clips, hooks, magnets, hook-and-loop assemblies, friction fit, etc.) and remain within the scope of the present disclosure.

The control system 30 may also include a light source 2 and a cell detector 9 for detecting the number of cells within the chamber 15, detecting the change in the number of cells within the chamber 15 or the like and reporting the results back to the control system 30. Additionally, the control system 30, via any suitable detection device, mechanism or method, may monitor the any suitable parameter involved in the growth of the target cells, for example and without limitation, the change in the number of target cells, pH, $CO_2$, glucose, calcium, potassium, sodium, temperature, humidity or any other suitable factor and adjust the frequency and/or speed of the movement of the agitator within the chamber and/or adjust the amount of media, the type of media, the amount of buffer, the type of buffer, the amount of $CO_2$, or make any other suitable adjustment based on any control system measurements so as to enhance or promote the growth of the target cells within the chamber 15.

The control system 30 is operable to cause the agitator to move within the interior 35 of the chamber 15. This may be accomplished a variety of ways. In the illustrative embodiment, the control system includes a motor 65 operable to rotate the chamber 15 between a first position and second position. As will be discussed below, the first position and second position are approximately 180° apart but it will be appreciated that first and second positions may have any suitable angular relationship relative to one another and remain within the scope of the present disclosure. The chamber 15 may be rotated in a horizontal plane, rotated in a vertical plans or rotated, shifted, slid or otherwise moved in any suitable mariner to cause the agitator 20 to move within the chamber 15.

In addition, the control system 30 may include first and second magnetic field generators 70, 72 for exciting the beads 21, or other agitator 20, so as to move the beads 21 within the chamber 15 to mix the target cells and culture media. In the illustrative embodiment, each magnetic field generator is an electromagnet that generates a magnetic field when energized and ceases to create a magnetic field when de-energized. When energized, each magnetic field generator draws the agitator 20, e.g. the beads 21, toward the energized magnetic field generator. In an alternative embodiment, a permanent magnet may be used wherein the control system 30 is operable to remove the magnet from the vicinity of the chamber 15 or otherwise block the magnetic field from the magnet from penetrating into the chamber 15. While the illustrative embodiment employs both chamber rotation and electromagnets for moving the agitator within the chamber, it will be appreciated that chamber rotation may be used alone or that electromagnets may be used alone. Moreover, it will be appreciated that any technique for moving the agitator within the chamber may be employed and remain within the scope of the present disclosure.

Referring now to FIG. 3, another embodiment of bioreactor for growing cells is shown. It includes a cell culture chamber (container) 19, a chamber rotation motor 21, a connect (axis) 18 between the cell culture chamber 19 and the chamber rotation motor 21, an axis 22 for the chamber position changes between vertical and horizontal. The entire bioreactor system also includes the remaining parts 2, 9, 8, 30, 55, 60 and 65 as shown in FIG. 1.

Figure 3A:
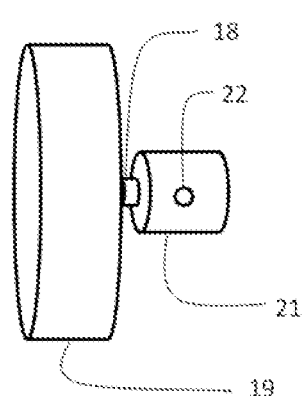
FIGS. 3a-3b shows a series of schematic views of a bioreactor with a cell culture container in the vertical rotation state (3a) and in the horizontal static state (3b).
Figure 3B:
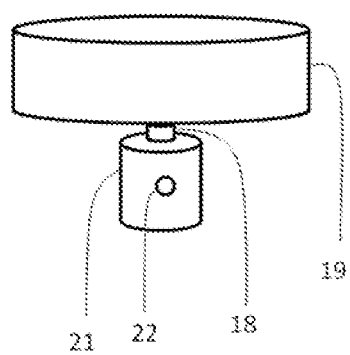

When the chamber 19 is in the vertical position, the chamber rotation motor 21 drives the chamber rotating in a certain speed (normally at 2-60 rpm) through connector 18 to keep cells in suspension state (FIG. 3a). When dynamic culture needs to stop, the motor (could be a servo 65 as shown in FIG. 1.) drives the chamber to change its position from vertical to horizontal through the axis 22. During the chamber position changes, its rotating speed gradually reduces to 0 rpm to minimize the inertial effects of the cells' moving on the cell distribution. Thus, when the chamber reaches the horizontal level (FIG. 3b), cells in suspension can freely fall down to the flat bottom of the chamber 19. Although the cell chamber in FIG. 3b faces up for the static culture, but other orientation, such as faces dawn, still remains within the scope of the present disclosure. Although it is appreciated to apply the ranges for the optimal speed of the rotation (2 rpm to 60 rpm), the range for the deceleration of the cell culture container ($-5$ $rpm^2$ to $-120$ $rpm^2$), the range for the ratio of the rotation speed/deceleration of the cell culture container rotation (1 to 160), and the range for the speed of container position change (0.1 to 60 rpm) for keep cells evenly distributed in static culture, all suitable speed of the rotation, deceleration of the cell culture container, ratio of the rotation speed/deceleration of the cell culture container rotation and speed of container position change for the cell even distribution in static culture following a dynamic culture remain within the scope of the present disclosure. Although the agitators, cell carriers and other supporting materials are not shown in FIGS. 3a and 3b, the application of these materials in this bioreactor system still remains within the scope of the present disclosure.

The invention claimed is:

1. A bioreactor system for cultivating cells in all three possible states; static, dynamic, or alternating between static and dynamic states, in which no cell-transferring between cell culture containers is needed during the alternating between the two culture states and all types of suspension cells, adherent cells, and partial adherent cells are evenly distributed in the static cell culture following a dynamic culture, comprising:

a cell culture container for cell growth which includes a cell culture chamber;

a cell detector for detecting cell density;

a first power set configured to rotate the cell culture container wherein the rotation can include a deceleration range between $-5$ $rpm^2$ to $-120$ $rpm^2$;

a second power set configured to adjust the culture container between a vertical orientation during the dynamic state and a horizontal orientation during the static state; and a computer system programmed to control the first power set and the second power set such that a suspension of cells can be evenly distributed in static state following dynamic state by controlling a speed of rotation of the container, a deceleration of the of the rotation of the container and a speed of the position change of the container from vertical to horizontal, wherein the deceleration has a range between $-5$ $rpm^2$ to $-120$ $rpm^2$.

2. The bioreactor system according to claim 1, wherein the computer system is further programmed such that a ratio of rotation speed/deceleration of the container is between 1 to 160.

3. The bioreactor system according to claim 1, wherein the cell culture container includes agitators or beads for cell suspension and adherent cell attachment.

4. The bioreactor system according to claim 1, wherein the computer system is further programmed such that the rotation speed has a range between 2 rpm and 60 rpm.

5. The bioreactor system according to claim 1, wherein the computer system is further programmed to provide static state, dynamic state and alternating between static and dynamic states.

6. The bioreactor system according to claim 1, wherein the computer system is further programmed to control the time, speed and frequency between the static and dynamic states.

7. The bioreactor system according to claim 1, wherein the cell detector includes a light source and a cell detector for detecting the cell number within the chamber and reporting the result to the computer system which is further programmed to make any suitable adjustment so as to enhance or promote the growth of target cells with the chamber.

8. The bioreactor system according to claim 1, wherein the computer system is further programmed such that the rotation speed has a range between 2 rpm and 60 rpm, a ratio of rotation speed/deceleration of the container is between 1 to 160, and the speed of the container position change has a range between 0.1 rpm to 60 rpm.

* * * * *